United States Patent [19]
Kwak et al.

[11] Patent Number: 5,178,143
[45] Date of Patent: Jan. 12, 1993

[54] ELECTRICALLY CONDUCTIVE GEL COMPOSITION

[75] Inventors: Yoon T. Kwak, Brooklyn, N.Y.; Stephen L. Kopolow, Plainsboro; Mohammed Tazi, Wayne, both of N.J.

[73] Assignee: ISP Investments Inc., Wilmington, Del.

[21] Appl. No.: 734,976

[22] Filed: Jul. 24, 1991

[51] Int. Cl.$^5$ .......................... A61B 5/04; A61N 1/04
[52] U.S. Cl. .................................... 128/639; 128/803; 252/500
[58] Field of Search ................................ 128/639–641, 128/708, 802, 803; 606/32; 252/500

[56] References Cited

U.S. PATENT DOCUMENTS

| | | | |
|---|---|---|---|
| 4,002,221 | 1/1977 | Buchalter | 252/500 X |
| 4,352,359 | 10/1982 | Larimore et al. | 128/640 |
| 4,699,146 | 10/1987 | Sieverding | 128/640 |
| 4,810,418 | 3/1989 | Burvee | 252/500 |

FOREIGN PATENT DOCUMENTS

| | | | |
|---|---|---|---|
| 0153838 | 8/1985 | Japan | 128/640 |
| 0153839 | 8/1985 | Japan | 128/640 |
| 3043646 | 2/1988 | Japan | 128/639 |
| 0092683 | 4/1988 | Japan | 252/500 |

*Primary Examiner*—Lee S. Cohen
*Attorney, Agent, or Firm*—Walter Katz; Marilyn J. Maue; Joshua J. Ward

[57] ABSTRACT

What is provided herein is an electrically conductive gel composition for use in establishing a low resistance contact between an electrode and a biological body, comprising a clear, aqueous solution of about 0.1 to 3% by weight of a crosslinked, neutralized copolymer of maleic anhydride and a $C_1$–$C_5$ alkyl vinyl ether. In the preferred form of the invention, the composition contains about 0.1 to 3% by weight of the crosslinked, neutralized copolymer which contains about 1 to 5 mole % based on the alkyl vinyl ether of a crosslinking agent.

4 Claims, No Drawings

ELECTRICALLY CONDUCTIVE GEL COMPOSITION

BACKGROUND OF THE INVENTION

1. Field of the Invention

The present invention relates generally to electrically conductive gels which are used to transmit an electrical signal between the human skin and an electrode attached to an electrical recording or stimulating device.

2. Description of the Prior Art

Frequently in the practice of medicine it is desirable to make electrical contact with the body. Such contact may be for the purpose of measuring electrical signals, as in the making of electrocardiograms or electroencephalograms, or applying electrical impulses to the body during electrotherapy.

The skin is a difficult structure with which to make reliable, low resistance, electrical contact. Accordingly, it has become customary in the art to utilize a conductive medium between the electrode and the skin to enhance conductivity. This medium normally takes the form of a conductive paste or gel which makes intimate contact with the skin, by conforming to the contours of the skin, and fills the gaps between the skin and the electrode, thus providing a more reliable path for the electrical current than is afforded by dry surface contact between electrode and skin. These gels or pastes are normally made of a thickened aqueous mixture containing a conductive salt, such as sodium chloride. Conventional thickening agents typically include polymers, such as polyvinylalcohol (commonly referred to as PVA), polyethylene glycol or polypropylene glycol; glycerol and glycerol derivatives, such as glycerol monostearate; and a number of naturally occurring gummy materials, such as gum tragacanth, sodium alginate, locust bean gum and guar gum. A number of synthetic gummy materials and thickeners have also been used, including carboxymethyl cellulose, and proprietary materials such as Gantrez ® materials sold by International Specialty Products Inc. and Carbopols ® sold by the B. F. Goodrich Co.

Examples of the gels or pastes of the prior art can be found in U.S. Pat. Nos. 4,016,869; 3,998,215; 3,989,050; 3,658,726; 3,265,638; and 4,406,827. These gels and creams are comprised of a thickened aqueous mixture and a salt or polarizing substance and do a reasonably effective job of making electrical contact with the skin. In particular, they make possible a contact which is largely free of voids and areas of poor or intermittent contact, which, when present, result in the generation of spurious electrical signals. Such spurious signals interfere with the collection of desired electrical data. However, all of these gels have one major disadvantage. They are sticky, messy materials which are unpleasant to use and are hard to remove from surfaces they have contacted. This problem has been addressed in the art by reinforcing the gelatinous or creamy conductive materials with porous or fibrous substances, which help to contain the gel or cream in a cohesive matrix, see U.S. Pat. No. 3,998,215. These structures, often referred to as gel pads, function well in regard to making good electrical contact with skin. However, the addition of nonconductive structural members within the conductive gel inevitably alters the resistance of a gel pad relative to that of the pure gel.

The gels of the present invention are an improvement over prior art gels. They maintain themselves as a cohesive mass without the need for mechanical reinforcement. They do not leave a residue on the skin or the electrode. Furthermore, they are capable of tolerating high concentrations of salt without breakdown of the gel. The gels of the present invention are less expensive to produce than the gels of the prior art since they can contain relatively less thickener and more water while still maintaining sufficient cohesive strength.

SUMMARY OF THE INVENTION

The present invention provides an electrically conductive gel for use in establishing a low resistance contact between an electrode and a biological body, comprising an aqueous solution of a crosslinked agent. The gum and crosslinking agent are present in quantities sufficient to impart a gel-like body to the material and to provide the electrically conductive gel with sufficient internal strength to remain cohesive without reinforcement. The gel material is capable of containing up to saturated concentrations of ionized salt without breakdown of the crosslinked gel. The gel material is non-sticky in character.

The gel of the instant invention proides a conductive, conformable interface between the skin and the electrodes placed thereon thus preventing electrical noise interference, and additionally is easy to apply, removable without leaving a residue, and has sufficient strength of itself to perform well without reinforcement.

Although approximately 99% water, the gel composition stays together in a cohesive mass rather than spreading and sticking to surfaces with which it comes in contact. In this connection "cohesive" should be interpreted to mean that the gel has more adhesion to itself than to the surface of the skin and, thus, is capable of maintaining internal integrity and lifting from the skin without leaving a residue.

The instant invention provides a gel which conducts small electrical signals faithfully and which produces no artifacts of its own to degrade the signal.

The gel is physically stable over a wide temperature range, i.e., its flow and cohesive properties are essentially the same over the range of 0° to 60° C.

The gel of the present invention is resistant to drying out.

The gel can be used on the skin routinely with a minimum of irritation to the skin.

The gels of the present invention can be used as a conductive medium on a patient's skin before emplacing an electrode or in a pre-assembled electrode. An example of the former use is in emergency situations where a patient is suffering from cardiac distress. Dabs of gel are dispensed onto the patient's skin in a standard pattern over the heart area. Electrodes are attached to these portions and are connected to an electrocardiograph, the read-out of which, commonly called an E.C.G., provides an indication of the patient's heart condition. For long-term monitoring of heart-function it is preferred to use the gel in a pre-assembled electrode, referred to as a "monitoring electrode". Such an electrode comprises an electrode plate having on one surface thereof means for electrical connection to an electromedical apparatus and on the opposite, body contacting surface thereof, the electrically conductive gel material of the present invention. In both uses the gel is applied and electrical contact achieved with light finger pressure. After use the gel may simply be lifted off the skin in a cohesive mass without leaving a sticky residue.

Although the gel of this invention is particularly useful as a conductive medium between the skin and a biopotential monitoring electrode suitable for detecting the very small electrical signals, such as are characteristic of E.C.G. measurements, it is not limited to this use. For example, the gel can be used as the conductive medium between defibrillation electrodes and the skin of a patient whose heart is in fibrillation. In such a case high voltages are required in order to electrically shock the heart into beating. A major advantage of the new gel in this use is that it does not smear or flow rapidly over a surface, thus avoiding the creation of a potentially dangerous conductive path; possibly over a patient's chest. An added advantage of the gel of the present invention is the greatly reduced chore of cleanup. Since the electrodes used in defibrillation are large, a substantial proportion of the patient's chest can become covered with conductive medium. The cohesive, non-sticky gel of the present invention greatly eases cleanup of the patient.

Another use of the present invention is as an electrically conductive medium for an electrosurgical ground plate. Still another use of the present gel is as the conductive medium between the skin and electrodes of the type used for transcutaneous nerve stimulation or for pain relief. These electrodes are often in the form of metal plates or foils.

It should be pointed out that while the gel can be used advantageously with electrosurgical grounding plates or with transcutaneous nerve stimulation electrodes, as described above, the preferred embodiment of the gel has limitations in conditions where it is under pressure. The compositions have the ability to cold flow; that is, when placed in a vessel the gum will eventually acquire the shape of the inside of the vessel. By this means, the ability of the gel to conform accurately to the contours of, for example, the skin and the undersurface of an electrode, is assured. In practice, a momentary light finger pressure is all that is required to emplace an electrode properly on the skin. However, due to its ability to cold flow, the gel will spread slowly under pressure, and if squeezed for along time, such as when placed under a supine patient undergoing lengthy surgery, it could be squeezed out beyond the immediate area of the electrode plate. Under these conditions, a restraining means can be used to keep the gel in place. A porous fibrous material, such as a pouch of inert porous woven or nonwoven fabric placed around the gel can be used as a restraining means. An open-cell foam, such as one of the polyurethane foams, impregnated with the gel may also be used.

SUMMARY OF THE INVENTION

What is provided herein is an electrically conductive gel composition for use in establishing a low resistance contact between an electrode and a biological body, comprising a clear, aqueous solution of about 0.1 to 3% by weight of a crosslinked, neutralized copolymer of maleic anhydride and a $C_1$-$C_5$ alkyl vinyl ether. In the preferred form of the invention, the composition contains about 0.25 to 1% by weight of the crosslinked, neutralized copolymer which contains about 1 to 5 mole % based on the alkyl vinyl ether of a crosslinking agent.

The polymerization process provides the crosslinked copolymer as a fine, white powder, in pumpable slurry form in the cosolvent system, which can be filtered and dried.

The resulting crosslinked copolymer then can be neutralized in aqueous solution with a suitable base such as sodium or potassium hydroxide, generally in a degree of neutralization which provides a pH of about 4–11. Such solutions will provide the desired clear gels for use in the composition of the invention.

Suitably, the electrically conductive gel composition of the invention comprises the crosslinked, neutralized copolymer gel in the form of a clear, aqueous solution containing about 0.1 to 3% by weight of the crosslinked, neutralized copolymer, preferably about 0.25 to 2%.

DETAILED DESCRIPTION OF THE INVENTION

The crosslinked, neutralized copolymer of maleic anhydride and a $C_1$-$C_5$ alkyl vinyl ether is prepared by slurry polymerization of the monomers in the presence of an organic free radical—generating initiator and a suitable amount of a crosslinking agent in a cosolvent system which is a mixture of a carboxylic acid ester and a saturated hydrocarbon, such as a mixture of ethyl acetate and cyclohexane, preferably in a weight ratio of about 35 to 55% ethyl acetate and 45 to 65% cyclohexane.

The amount of crosslinking agent generally present is about 1 to 5 mole percent based on the monovinyl alkyl ether component of the copolymer.

Suitable crosslinking agents include the divinyl ethers of an aliphatic diol, e.g. the divinyl ethers of 1,2-ethanediol, 1,3-propanediol, 1,4-butanediol, 1,5-pentanediol, 1,6-hexanediol, 1,7-heptanediol, 1,8-octanediol, 1,9-nonanediol, 1,10-decanediol, 1,11-unidecanediol, and 1,12-dodecanediol; the divinyl ethers of diethylene glycol, triethylene glycol, tetraethylene glycol, pentaethylene glycol, hexaethylene glycol, heptaethylene glycol, octaethylene glycol, nonaethylene glycol and decaethylene glycol, and other polyalkylene glycols having a molecular weight of up to about 5,900. Other suitable crosslinking agents include 1,7-octadiene; 1,9-decadiene; divinylbenzene; N,N'-bis-methylene acrylamide; acrylates such as polyethylene glycol diacrylate, trimethylolpropane triacrylate and propylene glycol diacrylate; and polyhydric alcohols esterified once or twice with acrylic acid, triallylamine, tetraallylethylenediamine, diallyl phthalate, and the like.

EXAMPLE 1

Preparation of Crosslinked Copolymer

A. A reactor was precharged with 550 g. of a 50:50 weight % mixture of ethyl acetate and cyclohexane as cosolvent system, and 1,9-decadiene as crosslinking agent. The reactor then was purged with nitrogen, heated to 58° C., and charged with initiator Lupersol-11 initiator (t-butyl peroxypivalate) at a 0.15 to 2% by weight level based on maleic anhydride monomer. Then 60 g. molten maleic anhydride and 47.6 g. methyl vinyl ether were fed separately (or through a common inlet) into the reactor over a 2 to 3 hour period. The reactants were held at 58° C. for an additional 1 to 3 hours, cooled, vented and discharged. The resulting slurry of the crosslinked copolymer product in the cosolvent at an 18 to 25% solids level was filtered and dried.

EXAMPLES 2-5

Preparation of Electrically Conductive Gel Compositions

2. The crosslinked copolymer of Example 1, 1 g., was neutralized with 2.6 g. of 10% NaOH in 96.4 g. of distilled water. The product was a crosslinked, neutralized gel composition having 1% polymer solids therein.

3. As above—0.75 g. polymer, 1.95 g. NaOH, 97.3 g. water—0.75% polymer.

4. As above—0.5 g. polymer, 1.3 g. NaOH, 98.2 g. water—0.5% polymer.

5. The procedure above was repeated with 0.25 g. polymer, 0.65 g. 10% NaOH, and 99.1 g. water. The product contained 0.25% polymer.

EXAMPLE 6

Electrical Properties of Gel Compositions of Invention

| Test Sample | Electrical Resistance (ohms) |
| --- | --- |
| Invention - Exs. 2,3,4,5 | 220, 390, 450, 780 |
| STAODYN Gel | 880 |
| Carbopol 980 (0.5%) | 1650 |
| Carbopol 940 (0.5%) | 1750 |

Electrical resistivity was measured using a ⅜ inch thick plastic container which was uniformly filled with the test sample, electrical probes mounted in the sample, and the resistance between the electrical probes was measured.

The results show that the gel composition of the invention exhibits substantially lower electrical resistance than commercial gel compositions for the same use.

EXAMPLE 7

Stimulation of Nervous System

Transcutaneous Electrical Nerve Stimulation (TENS) is an electrical device for relieving pain which functions by delivering mild electrical signals through the skin to underlying nerves which then act on the nervous system to relieve the pain. A TENS Model Staodyn 4500M stimulator was used to test the effectiveness of conductive gel compositions for effective nerve stimulation through an affected skin area. Accordingly, sufficient gel composition was applied to cover the entire surface of the electrode of the device, the electrode was placed on the area to be stimulated, and tape was used. To secure the electrode to the skin the intensity was measured at a pulse rate of 100 Hz. The gel composition of Example 2 showed an intensity level of 4.0 whereas Staodyn conductive gel gave an intensity reading of 4.5, which indicates stronger stimulation with the electrically conductive gel composition of this invention as compared to commercially available materials.

While the invention has been described with particular reference to certain embodiments thereof, it will be understood that changes and modifications may be made which are within the skill of the art. Accordingly, it is intended to be bound only by the following claims, in which:

What is claimed is:

1. An electrically conductive gel composition for use in establishing a low resistance contact between an electrode and a biological body, comprising a clear, aqueous solution of about 0.1 to 3% by weight of a crosslinked, neutralized copolymer of maleic anhydride and a $C_1$-$C_5$ alkyl vinyl ether.

2. The electrically conductive gel composition of claim 1, which contains about 0.25 to 2% by weight of said crosslinked, neutralized copolymer.

3. The electrically conductive gel composition of claim 1, which is crosslinked with about 1 to 5 mole percent based on the alkyl vinyl ether of a crosslinking agent.

4. The electrically conductive gel composition of claim 1 which has a pH of 4-11.

* * * * *